(12) United States Patent
Ishida et al.

(10) Patent No.: US 9,138,438 B2
(45) Date of Patent: Sep. 22, 2015

(54) METHOD FOR PROTECTING A RETINAL NEURONAL CELL

(75) Inventors: Naruhiro Ishida, Ikoma (JP); Atsushi Shimazaki, Ikoma (JP)

(73) Assignees: ASAHI GLASS COMPANY, LIMITED, Tokyo (JP); SANTEN PHARMACEUTICAL CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 13/199,598

(22) Filed: Sep. 2, 2011

(65) Prior Publication Data

US 2012/0010288 A1   Jan. 12, 2012

Related U.S. Application Data

(62) Division of application No. 11/887,037, filed as application No. PCT/JP2006/306826 on Mar. 31, 2006, now abandoned.

(30) Foreign Application Priority Data

Mar. 31, 2005   (JP) ................................ 2005-100348

(51) Int. Cl.
*A61K 31/5575* (2006.01)
(52) U.S. Cl.
CPC .................................. *A61K 31/5575* (2013.01)
(58) Field of Classification Search
None
See application file for complete search history.

(56) References Cited

U.S. PATENT DOCUMENTS

| | | | |
|---|---|---|---|
| 4,599,353 A | 7/1986 | Bito | |
| 4,822,820 A | 4/1989 | DeSantis et al. | |
| 5,773,471 A | 6/1998 | Oguchi et al. | |
| 5,877,211 A | 3/1999 | Woodward | |
| 5,886,035 A * | 3/1999 | Shirasawa et al. | 514/530 |
| 5,985,920 A * | 11/1999 | Shirasawa et al. | 514/530 |
| 6,225,348 B1 * | 5/2001 | Paulsen | 514/530 |
| 6,242,485 B1 * | 6/2001 | Ueno | 514/530 |
| 6,451,787 B1 * | 9/2002 | Nakata et al. | 514/211.08 |
| 2002/0025985 A1 | 2/2002 | Ueno et al. | |
| 2003/0105133 A1 | 6/2003 | Bigge et al. | |
| 2004/0102437 A1 | 5/2004 | Takami et al. | |
| 2004/0106646 A1 | 6/2004 | Takayama et al. | |
| 2004/0138286 A1 | 7/2004 | Imazaki et al. | |

FOREIGN PATENT DOCUMENTS

| | | |
|---|---|---|
| EP | 0 850 926 A2 | 7/1998 |
| EP | 1 403 255 A1 | 3/2004 |
| JP | 59-1418 A | 1/1984 |
| JP | 3-501025 A | 3/1991 |
| JP | 8-501310 A | 2/1996 |
| JP | 9-87179 A | 3/1997 |
| JP | 10087607 A | 4/1998 |
| JP | 10-182465 A | 7/1998 |
| JP | 10-259179 A | 9/1998 |
| JP | 251225 A | 9/1998 |
| JP | 11-71344 A | 3/1999 |
| JP | 2001-072591 A | 3/2001 |
| JP | 2001-523721 A | 11/2001 |
| JP | 2002-293771 A | 10/2002 |
| JP | 2003-146904 A | 5/2003 |
| JP | 2003-527430 A | 9/2003 |
| JP | 2003-321442 A | 11/2003 |
| JP | 2004-2462 A | 1/2004 |
| WO | WO 90/02553 A1 | 3/1990 |
| WO | WO 94/06433 A1 | 3/1994 |
| WO | WO 98/12175 A1 | 3/1998 |
| WO | 01/56606 A1 | 8/2001 |
| WO | 01/56988 A1 | 8/2001 |
| WO | WO 02/22131 A1 | 3/2002 |
| WO | 02/083175 A1 | 10/2002 |
| WO | 02/100833 A1 | 12/2002 |
| WO | 03/004058 A1 | 1/2003 |
| WO | 2005/035506 A1 | 4/2005 |

OTHER PUBLICATIONS

"Evaluation of the Glaucomatous Damage on Retinal Nerve Fiber Layer Thickness Measured by Optical Coherence Tomography" by Kanamori et al., Am. J. Ophthalmol. 135, 513-20 (2003).*
"The Eye: II. Receptor and Neural Function of the Retina" by Guyton & Hall in Textbook of Medical Physiology, 9th Ed., W.B. Saunders Co (Philadelphia), pp. 637-38 (1996).*
"Progression of visual field loss in untreated glaucoma patients and suspects in St Lucia, West Indies." by Wilson, Trans. Am. Ophthalmol. Soc. 100, 365-410 (2002).*
"Chronic retinal vein occlusion in glaucoma" by Hitchings et al., Br. J. Ophthalmol. 60, 694-99 (1976).*
"Ischaemic optic neuropathy in chronic simple glaucoma" by Begg et al., Br. J. Ophthalmol. 55, 73-90 (1971).*
"Primary angle glaucoma and retinitis pigmentosa" by Badeeb et al., Acta Ophthalmol. (Copenh.) 71, 727-32 (PubMed Abstract No. 8154244) (1993).*
"Doxium (calcium dobesilate) reduces blood hyperviscosity and lowers elevated intraocular pressure in patients with diabetic retinopathy and glaucoma" by Vojnikovic, Ophthalmic Res. 23, 12-20 (PubMed Abstract 1870835) (1991).*
"The prevalence of macular degeneration in a cohort of institutionalized geriatric glaucoma patients" by Peräsalo, Acta Ophthalmol. (Copenh). 72, 175-77 (PubMed Abstract 8079621) (1994).*
Hayami Kayoko et al., "Photoreceptor Protection Against Constant Light-Induced Damage by Isopropyl Unoprostone, a Prostaglandin $F_{2\alpha}$ Metabolite-Related Compound," *Ophthalmic Research*, 2001, vol. 33, No. 4, pp. 203 to 209.

(Continued)

*Primary Examiner* — Theodore R West
(74) *Attorney, Agent, or Firm* — Holtz, Holtz, Goodman & Chick PC

(57) ABSTRACT

A method of protecting a retinal neuronal cell by administering an effective amount of a prostaglandin F2α derivative to a patient. A method of preventing or treating an eye disease associated with retinal neuronal cell damage by administering a therapeutically effective amount of a prostaglandin F2α derivative to a patient.

11 Claims, 1 Drawing Sheet

(56) References Cited

OTHER PUBLICATIONS

Drago Filippo et al., "Latanoprost Exerts Neuroprotective Activity In Vitro and In Vivo," *Experimental Eye Research*, 2001, vol. 72, No. 4, pp. 479 to 486.

Yaniv Barkana et al., "Neuroprotection in Ophthalmology: A Review," *Brain Research Bulletin*, 62, (2004), pp. 447 to 453.

Abbott F. Clark et al., "Ophthalmic Drug Discovery," *Nature Review*, vol. 2, (2003), pp. 448 to 459.

Kitaoka Y. et al., "Involvement of RhoA and possible neuroprotective effect of fasudil, a Rho kinase inhibitor, in NMDA-induced neurotoxicity in the rat retina," *Brain Research*, 20040820 NL, vol. 1018, No. 1, Aug. 20, 2004, pp. 111 to 118.

Monnier P.P. et al., "The Rho/ROCK pathway mediates neurite growth-inhibitory activity associated with the chondroitin sulfate proteoglycans of the CNS glial scar," *Molecular and Cellular Neuroscience*, Mar. 1, 2003 US, vol. 22, No. 3, pp. 319 to 330.

Kudo et al., "Latanoprost prevents retinal ganglion cell death induced by N-methyl-D-aspartame or optic nerve laxotomy," *Invest. Ophthalmol. Vis. Sci.*, (2004), 45, Abstract 881, 881-B854.

Nakajima et al., "New Fluoroprostaglandin F2alpha Derivatives with Prostanoid FP-Receptor Agonistic Activity as Potent Ocular-Hypotensive Agents," *Biol. Pharm. Bull.*, 26, (2003), pp. 1691-1695.

\* cited by examiner

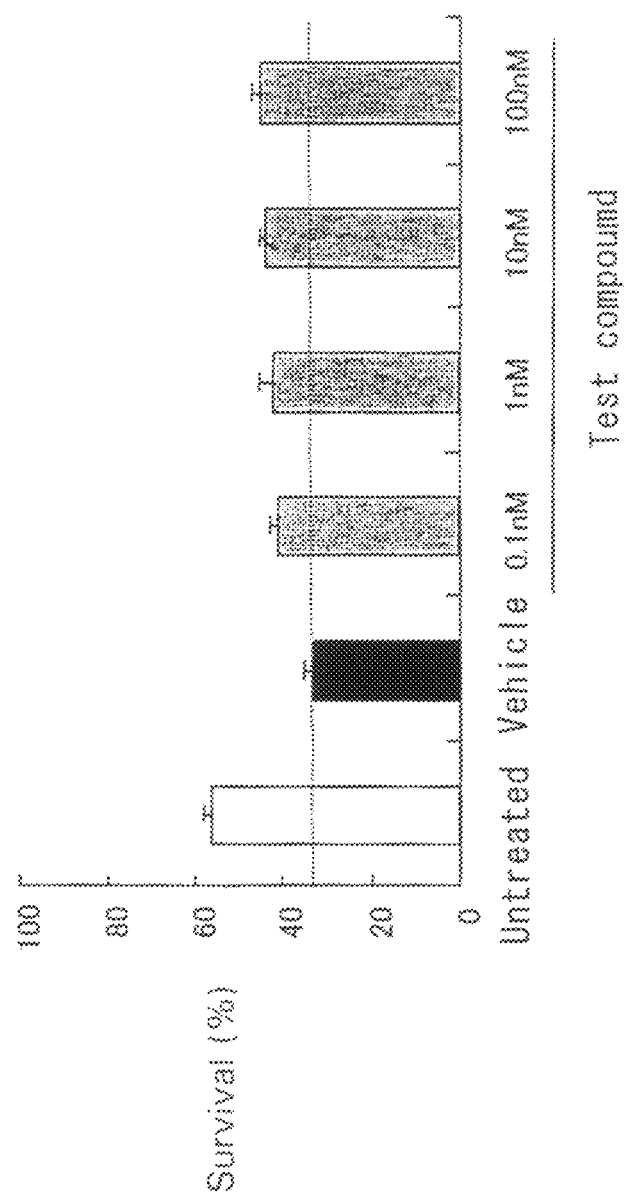

METHOD FOR PROTECTING A RETINAL NEURONAL CELL

CROSS-REFERENCE TO RELATED APPLICATIONS

This application is a divisional application of application Ser. No. 11/887,037 (abandoned) filed Sep. 24, 2007, which is the United States national phase application under 35 USC 371 of International application PCT/JP2006/306826 filed Mar. 31, 2006. The entire contents of each of application Ser. No. 11/887,037 and International application PCT/JP2006/306826 are hereby incorporated by reference herein.

TECHNICAL FIELD

The present invention relates to a protective agent for a retinal neuronal cell containing a prostaglandin F2α derivative as an active ingredient.

BACKGROUND ART

The retina is a tissue with a thickness of from 0.1 to 0.5 mm consisting of ten layers of inner limiting membrane, nerve fiber layer, ganglion cell layer, inner plexiform layer, inner nuclear layer, outer plexiform layer, outer nuclear layer, outer limiting membrane, photoreceptor cell layer and retinal pigment epithelium layer, and retinal neuronal cell groups including photoreceptor cells, bipolar cells, ganglion cells, horizontal cells, amacrine cells and Muller cells are present therein.

The retinal neuronal cells play an important role in the reception and transmission of visual information such as converting light stimulation into an electrical signal and transmitting the signal to the brain.

To specifically describe the mechanism of such transmission, the visual information from the eyes is converted into an electrical signal through photoreceptor cells and transmitted to ganglion cells by way of horizontal cells, bipolar cells and/or amacrine cells. Then, the electrical signal is transmitted to the brain by way of the optic nerve which is a bundle of optic nerve fibers including axons of ganglion cells.

On the other hand, when these retinal neuronal cells are damaged due to various causes, the homeostasis (a function to supply oxygen or nutrition to retinal neuronal cells through retinal blood circulation, and the like) of retinal neuronal cells cannot be maintained, and the transmission of visual information to the brain is inhibited. For example, it is widely known that dysfunction of retinal neuronal cells is caused in various retinal diseases such as retinal vascular occlusion, diabetic retinopathy, ischemic optic neuropathy, glaucoma, macular degeneration, retinitis pigmentosa and Leber's disease (Brain Res. Bull., 62(6), 447-453 (2004)).

It has recently been considered that retinal neuronal cell death due to retinal ischemia is one of the causes of retinal neuronal cell damage, and the following events have been reported regarding the retinal neuronal cell death due to retinal ischemia (JP-A-2003-146904 and Nature Rev., 2, 448-459 (2003)).

1) The mechanism of retinal neuronal cell death due to retinal ischemia is similar to that of cerebral neuronal cell death due to cerebral ischemia.

2) In short term retinal ischemia, the retinal inner layer (inner plexiform layer) is selectively damaged.

3) The excess release of glutamate during retinal ischemia can be observed.

4) By injecting an excitatory amino acid such as glutamate into the vitreous body, retinal neuronal cell death is induced.

5) The overstimulation mediated by retinal N-methyl-D-aspartate (NMDA) receptors promotes calcium (Ca) influx into cells, which results in inducing cell damage by way of induction of nitrogen monoxide (NO).

From these events, it is considered that a drug such as a glutamate neurotoxicity inhibitor, an NMDA receptor antagonist or an NO synthesis inhibitor is useful for treating an eye disease caused by retinal neuronal cell damage, and various studies have been carried out.

For example, JP-A-2001-072591 discloses a protective agent for a retinal neuronal cell containing nipradilol which is one of the β-blockers as an active ingredient. WO 01/056606 discloses a protective agent for an optic ganglion cell containing an interleukin-1 receptor antagonist protein as an active ingredient. WO 03/004058 discloses a protective agent for an optic ganglion cell containing an $α_1$ receptor antagonist such as brimonidine hydrochloride as an active ingredient. Experimental Eye Res., 72, 479-486 (2001) discloses a nerve-protecting effect of latanoprost which is one of the prostaglandin derivatives, etc.

On the other hand, prostaglandin F2α derivatives are disclosed as a therapeutic agent for glaucoma having an intraocular pressure lowering action in JP-A-59-1418, JP-T-3-501025, JP-T-8-501310, JP-A-10-182465, WO 98/12175, European Patent Application Publication No. 850926, JP-A-2004-002462, JP-A-10-259179, JP-A-2002-293771 and JP-A-2003-321442. JP-A-59-1418 discloses a natural prostaglandin F2α derivative. JP-T-3-501025 discloses a latanoprost-related compound. JP-T-8-501310 discloses a bimatoprost-related compound. JP-A-10-182465 discloses a travoprost-related compound. WO 98/12175 discloses a monofluoroprostaglandin F2α derivative. European Patent Application Publication No. 850926 and JP-A-2004-002462 disclose a difluoroprostaglandin F2α derivative. JP-A-10-259179 discloses a fluorine-containing prostaglandin F2α derivative having a multisubstituted aryloxy group. JP-A-2002-293771 discloses an ether type difluoroprostaglandin F2α derivative. JP-A-2003-321442 discloses a difluoroprostaglandin F2α amide derivative.

However, any of these documents does not describe an effect of a fluorine-containing prostaglandin F2α derivative on protecting a retinal neuronal cell at all.

DISCLOSURE OF THE INVENTION

Problems to be Solved

It is a very interesting subject to find a new pharmaceutical application of a prostaglandin F2α derivative (particularly a fluorine-containing prostaglandin F2α).

Means of Solving Problems

Accordingly, the present inventors made intensive studies in order to find a new pharmaceutical application of a prostaglandin F2α derivative. As a result, they found that the prostaglandin F2α derivative inhibits glutamate-induced retinal neuronal cell death in a concentration-dependent manner in rat fetal retinal neuronal cells, in other words, the prostaglandin F2α derivative acts directly on the retinal neuronal cells and exhibits a protective effect, thus accomplished the present invention.

The present invention relates to a protective agent for a retinal neuronal cell containing a prostaglandin F2α derivative as an active ingredient.

Further, the present invention relates to a method of protecting a retinal neuronal cell and a method of preventing or treating an eye disease associated with retinal neuronal cell damage.

In the present invention, the "prostaglandin F2α derivative" means a prostaglandin F2α-related compound derived from the skeleton of prostanoic acid.

Specifically, a protective agent for a retinal neuronal cell is, for example, one which contains a prostaglandin F2α derivative or a salt thereof such as a natural prostaglandin F2α derivative disclosed in JP-A-59-1418, a latanoprost-related compound (with the proviso that a latanoprost-related compound or a salt thereof excluding latanoprost) disclosed in JP-T-3-501025, a bimatoprost-related compound (preferably bimatoprost or a salt thereof) disclosed in JP-T-8-501310, a travoprost-related compound (preferably travoprost or a salt thereof) disclosed in JP-A-10-182465, or a fluorine-containing prostaglandin F2α derivative disclosed in WO 98/12175, European Patent Application Publication No. 850926, JP-A-2004-002462, JP-A-10-259179, JP-A-2002-293771 or JP-A-2003-321442 as an active ingredient.

Preferably, a protective agent for a retinal neuronal cell is, for example, one which contains a "fluorine-containing prostaglandin F2α derivative" as an active ingredient. The "fluorine-containing prostaglandin F2α derivative" means a prostaglandin F2α derivative having one or more fluorine atoms.

Specifically, a protective agent for a retinal neuronal cell is, for example, one which contains a fluorine-containing prostaglandin F2α derivative disclosed in WO 98/12175, European Patent Application Publication No. 850926, JP-A-2004-002462, JP-A-10-259179, JP-A-2002-293771 or JP-A-2003-321442 as an active ingredient.

More preferably, a protective agent for a retinal neuronal cell is, for example, one which contains a 15,15-difluoroprostaglandin F2α derivative disclosed in European Patent Application Publication No. 850926, JP-A-2004-002462, JP-A-10-259179, JP-A-2002-293771 or JP-A-2003-321442 as an active ingredient.

A further more preferred protective agent for a retinal neuronal cell is, for example, one which contains a 15,15-difluoroprostaglandin F2α derivative represented by the following general formula (1), which is a further more preferred fluorine-containing prostaglandin F2α derivative or a salt thereof, as an active ingredient.

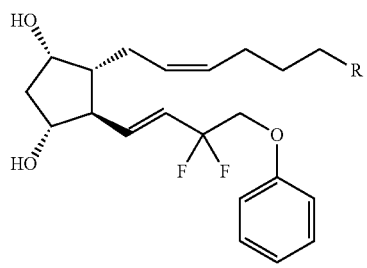

(1)

[R represents a hydroxyalkyl group, a formyl group, a carboxy group, an alkoxycarbonyl group, an aryloxycarbonyl group, an aminocarbonyl group, an alkylaminocarbonyl group or an arylaminocarbonyl group, and when R is an aryloxycarbonyl group or an arylaminocarbonyl group, the aryl moiety thereof may have a substituent. Hereinafter the same shall apply.]

The respective groups and terms defined in this specification will be shown below.

The "halogen" refers to fluorine, chlorine, bromine or iodine.

The "alkyl" refers to straight-chain or branched alkyl having 1 to 6 carbon atoms. Specific examples thereof include methyl, ethyl, n-propyl, n-butyl, n-pentyl, n-hexyl, isopropyl, isobutyl, sec-butyl, tert-butyl, isopentyl and the like.

The "alkoxy" refers to straight-chain or branched alkoxy having 1 to 6 carbon atoms. Specific examples thereof include methoxy, ethoxy, n-propoxy, n-butoxy, n-pentyloxy, n-hexyloxy, isopropoxy, isobutoxy, sec-butoxy, tert-butoxy, isopentyloxy and the like.

The "aryl" refers to monocyclic aromatic hydrocarbon, or bicyclic or tricyclic condensed polycyclic aromatic hydrocarbon having 6 to 14 carbon atoms. Specific examples thereof include phenyl, naphthyl, anthryl, phenanthryl and the like.

The "aryloxy" refers to monocyclic aromatic hydrocarbonoxy, or bicyclic or tricyclic condensed polycyclic aromatic hydrocarbonoxy having 6 to 14 carbon atoms. Specific examples thereof include phenoxy, naphthyloxy, anthryloxy, phenanthryloxy and the like.

The "alkylamino" refers to monoalkylamino or dialkylamino having 1 to 12 carbon atoms. Specific examples thereof include methylamino, ethylamino, dimethylamino, dihexylamino and the like.

The "arylamino" refers to monoarylamino or diarylamino having 6 to 28 carbon atoms. Specific examples thereof include phenylamino, naphthylamino, methylphenylamino, ethylphenylamino, diphenylamino, dianthrylamino and the like.

In the case where R is an "aryloxycarbonyl group" or an "arylaminocarbonyl group", the aryl moiety thereof may have a substituent. As the substituent, an atom or a group selected from a halogen atom, an alkyl group, a halogenated alkyl group and an alkoxy group is preferred, and the number of the substituents is preferably 1 to 3.

A further more preferred fluorine-containing prostaglandin F2α derivative is, for example, a 15,15-difluoroprostaglandin F2α derivative of the above-mentioned general formula (1) in which R represents a carboxy group or a salt group thereof or an alkoxycarbonyl group.

A particularly preferred fluorine-containing prostaglandin F2α derivative is, for example, a 15,15-difluoroprostaglandin F2α derivative of the above-mentioned general formula (1) in which R represents a carboxy group or a salt group thereof or an isopropoxycarbonyl group.

In addition, another preferred compound is, for example, a 15-monofluoroprostaglandin F2α derivative described in the above-mentioned WO 98/12175.

These prostaglandin F2α derivatives can be in the form of a salt with an inorganic acid such as hydrochloric acid, hydrobromic acid, hydroiodic acid, nitric acid, sulfuric acid or phosphoric acid, an organic acid such as acetic acid, fumalic acid, maleic acid, succinic acid or citric acid, an alkali metal such as lithium, sodium or potassium, an alkaline earth metal such as calcium or magnesium, ammonia or the like. These salts are also included in the present invention.

In the present invention, the "retinal neuronal cell" means a neuronal cell involved in the transmission of visual signal to the brain. Specifically, it means a photoreceptor cell, a horizontal cell, a bipolar cell, an optic ganglion cell, an amacrine cell or the like.

In the present invention, the "eye disease" means an eye disease associated with retinal neuronal cell damage. Specifically, it means abnormal visual field, retinal vascular occlusion, diabetic retinopathy, ischemic optic neuropathy, glaucoma, macular degeneration, retinitis pigmentosa, Leber's disease or the like, and preferably it means abnormal visual field, retinal vascular occlusion, diabetic retinopathy, ischemic optic neuropathy, macular degeneration, retinitis pigmentosa or Leber's disease.

The protective agent for a retinal neuronal cell of the present invention can be administered orally or parenterally. Examples of the dosage form for administration include an eye drop, an ophthalmic ointment, an injection, a tablet, a capsule, a granule, a powder, and the like, and particularly preferred is an eye drop. Such a preparation can be prepared by any of widely used techniques, for example, a technique disclosed in JP-A-59-1418, JP-T-3-501025, JP-T-8-501310, JP-A-10-182465, WO 98/12175, European Patent Application Publication No. 850926, JP-A-2004-002462, JP-A-10-259179, JP-A-2002-293771, JP-A-2003-321442, WO 02/22131 or the like.

For example, an eye drop can be prepared using a tonisity agent such as sodium chloride or concentrated glycerin, a buffer such as sodium phosphate or sodium acetate, a surfactant such as polyoxyethylene sorbitan monooleate, polyoxyl 40 stearate or polyoxyethylene hydrogenated castor oil, a stabilizer such as sodium citrate or sodium edetate, a preservative such as benzalkonium chloride or paraben according to need. The pH of the eye drop is permitted as long as it falls within the range that is acceptable as an ophthalmic preparation. Preferred pH is in the range of from 4 to 8.

An ophthalmic ointment can be prepared using a widely used base such as white soft paraffin or liquid paraffin according to need.

Further, an oral preparation such as a tablet, capsule, a granule or a powder can be prepared using an extender such as lactose, crystalline cellulose, starch or a vegetable oil, a lubricant such as magnesium stearate or talc, a binder such as hydroxypropyl cellulose, or polyvinylpyrrolidone, a disintegrant such as carboxymethyl cellulose calcium or low-substituted hydroxypropylmethyl cellulose, a coating agent such as hydroxypropylmethyl cellulose, macrogol or a silicone resin, a film forming agent such as gelatin film, or the like according to need.

The dose can be appropriately selected depending on the symptoms, age, dosage form and the like. An eye drop may be instilled once to several times a day at a concentration of from 0.00001 to 1% (w/v), preferably from 0.0001 to 1% (w/v). An oral preparation may be administered once or divided into several times at a dose of generally from 0.01 to 5000 mg per day, preferably from 0.1 to 1000 mg per day.

Advantage of the Invention

As will be described in detail in the section of Pharmacological Test below, an effect of a prostaglandin F2α derivative on glutamate-induced retinal neuronal cell death was examined using rat fetal retinal neuronal cells. As a result, the prostaglandin F2α derivative inhibited the glutamate-induced retinal neuronal cell death in a concentration-dependent manner. That is, the prostaglandin F2α derivative has an action of protecting a retinal neuronal cell, and is useful for the prevention or treatment of an eye disease associated with retinal neuronal cell damage.

BEST MODE FOR CARRYING OUT THE INVENTION

Hereinafter, preparation examples of the present invention and results of a pharmacological test will be described. However, these examples are described for the purpose of understanding the present invention better and are not meant to limit the scope of the present invention.

Preparation Examples

Hereinafter, examples of general preparations containing a prostaglandin F2α derivative according to the present invention will be described.

| 1) Eye drop (in 100 mL) | |
|---|---|
| Prostaglandin F2α derivative | 10 mg |
| Concentrated glycerin | 2500 mg |
| Polysorbate 80 | 2000 mg |
| Sodium phosphate monobasic dihydrate | 200 mg |
| Sterile purified water | q.s. |
| 1N hydrochloric acid or 1N sodium hydroxide | q.s. |
| pH | 6.0 |

A desired eye drop can be obtained by appropriately changing the kinds and the amounts of the prostaglandin F2α derivative and additives.

| 2) Ophthalmic ointment (in 100 g) | |
|---|---|
| Prostaglandin F2α derivative | 0.1 g |
| Liquid paraffin | 20 g |
| White soft paraffin | 77.9 g |
| Purified lanolin | 2 g |

A desired ophthalmic ointment can be obtained by appropriately changing the kinds and the amounts of the prostaglandin F2α derivative and additives.

[Pharmacological Test]

In order to find a new pharmaceutical application of a prostaglandin F2α derivative, by using rat fetal retinal neuronal cells, an effect of a prostaglandin F2α derivative on protecting retinal neuronal cells against glutamate-induced retinal neuronal cell death was evaluated and examined.

Incidentally, as the prostaglandin F2α derivative which is a test compound, 16-phenoxy-15-deoxy-15,15-difluoro-17,18,19,20-tetranor-prostaglandin F2α was used.

(1) Isolation Culture of Retinal Neuronal Cells

A pregnant SD rat was subjected to laparotomy under systemic anesthesia, and the uterus was transferred to a dish containing Hanks's balanced salt solution (HBSS). A rat fetus was isolated from the uterus, and the eyeballs of the rat fetus were taken out. The retina was isolated from the eyeballs under a stereoscopic microscope and cut into pieces with a surgical knife. Then, the retina was further broken down to the cellular level and passed through a nylon mesh (No. 305, manufactured by NBC Industries Co., Ltd.) to remove cell aggregates, and then, the resulting filtrate was centrifuged at 1000 rpm for 4 minutes. The supernatant was removed, and an appropriate amount of a modified Eagle's medium (MEM) containing 10% fetal bovine serum (FBS) was added to the remaining cells to suspend them. After the cell number was counted with a hemocytometer, an MEM medium containing 10% FBS was added thereto, whereby a cell suspension with a cell density of $0.8 \times 10^6$ cells/mL was obtained. The cell suspension was inoculated in an amount of 80 μL each into polyethylenimine-coated plastic discs, and the discs were allowed to stand in an incubator (37° C., 5% $CO_2$). The day of cell inoculation was designated as day 1 of culture, and medium replacement was carried out on even number days. Incidentally, up to day 4, an MEM medium containing 10% FBS was used, and after day 8, an MEM medium containing 10% horse serum (HS) was used. Incidentally, on day 6, 6 mL of a medium containing cytarabine (Ara-C) ($1.5 \times 10^{-5}$ M in an MEM medium containing 10% FBS) was used for removing proliferative cells.

(2) Preparation of HS-Containing MEM Medium Containing Test Compound 2 mg of the test compound was dissolved in 100% ethanol, and the resulting solution was sequentially diluted with an HS-containing MEM medium, whereby an HS-containing MEM medium containing the test compound at 0.1 nM, 1 nM, 10 nM or 100 nM was prepared.

(3) Preparation of Serum-Free MEM Medium Containing Test Compound 2 mg of the test compound was dissolved in 100% ethanol, and the resulting solution was sequentially diluted with a serum-free MEM medium, whereby a serum-free MEM medium containing the test compound at 0.1 nM, 1 nM, 10 nM or 100 nM was prepared.

(4) Evaluation of Cell Death

At day 10 of culture, the plastic discs in which cells were inoculated and cultured were transferred to the HS-containing MEM medium containing the test compound and incubated for 24 hours (37° C., 5% $CO_2$). The plastic discs were transferred to a serum-free MEM medium containing 1 mM glutamate and incubated for 10 minutes, and then transferred to the serum-free MEM medium containing the test compound and incubated for 1 hour (37° C., 5% $CO_2$). Then, the cells were stained with a 1.5% trypan blue solution for 10 minutes and fixed by adding a 10% formalin fixative solution thereto. After the cells were washed with a physiological saline solution, stained cells and unstained cells were counted under an inverted microscope.

Incidentally, a vehicle administration group was prepared by carrying out the same test as described above except that an HS-containing MEM medium was used instead of the above-mentioned HS-containing MEM medium containing the test compound and a serum-free MEM medium was used instead of the above-mentioned serum-free MEM medium containing the test compound.

Further, an untreated group was prepared by carrying out the same test as described above except that an HS-containing MEM medium was used instead of the above-mentioned HS-containing MEM medium containing the test compound and a serum-free MEM medium was used instead of the above-mentioned serum-free MEM medium containing the test compound, and further a treatment with a serum-free MEM medium containing glutamate was not carried out.

The survival rate was calculated based on the following calculation equation.

Survival rate (%)={(unstained cell number)/(unstained cell number+stained cell number)}×100

(5) Results and Discussion

As shown in FIG. 1, about 40% cell death of the retinal neuronal cells due to the treatment with glutamate was observed in the vehicle addition group. However, when the HS-containing MEM medium containing the test compound (0.1 nM to 100 nM) was used as a medium, the glutamate-induced retinal neuronal cell death was inhibited in a concentration-dependent manner, and it was confirmed that the test compound has an action of protecting a retinal neuronal cell.

BRIEF DESCRIPTION OF THE DRAWING

FIG. 1 is a graph showing the survival rate for each concentration in the case of using the test compound by the addition of glutamate.

What is claimed is:

1. A method for treating an eye disease selected from the group consisting of abnormal visual field, retinal vascular occlusion, diabetic retinopathy, ischemic optic neuropathy, macular degeneration, retinitis pigmentosa and Leber's disease, the method comprising administering to a patient in need thereof, wherein the patient does not have glaucoma, a therapeutically effective amount of a 15,15-difluoroprostaglandin F2α derivative is a compound represented by the following formula (1) or a salt thereof:

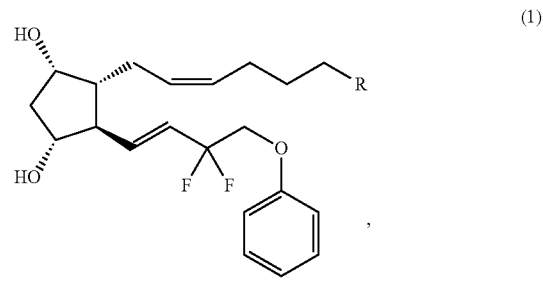

(1)

wherein R represents a hydroxyalkyl group, a formyl group, a carboxy group, an isopropoxycarbonyl group, an alkoxycarbonyl group, an aryloxycarbonyl group, an aminocarbonyl group, an alkylaminocarbonyl group or an arylaminocarbonyl group, and when R is an aryloxycarbonyl group or an arylaminocarbonyl group, the aryl moiety thereof may have a substituent.

2. The method according to claim 1, wherein in the formula (1), R represents a carboxy group or a salt group thereof or an alkoxycarbonyl group.

3. The method according to claim 1, wherein in the formula (I), R represents a carboxy group or a salt thereof or an isopropoxycarbonyl group.

4. The method according to claim 1, wherein the compound is 16-phenoxy-15-deoxy-15,15-difluoro-17,18,19,20-tetranor-prostaglandin F2α.

5. The method according to claim 1, wherein the disease is abnormal visual field.

6. The method according to claim 1, wherein the disease is retinal vascular occlusion.

7. The method according to claim 1, wherein the disease is diabetic retinopathy.

8. The method according to claim 1, wherein the disease is ischemic optic neuropathy.

9. The method according to claim 1, wherein the disease is macular degeneration.

10. The method according to claim 1, wherein the disease is retinitis pigmentosa.

11. The method according to claim 1, wherein the disease is Leber's disease.

* * * * *